(12) United States Patent
Lieber et al.

(10) Patent No.: US 9,541,522 B2
(45) Date of Patent: Jan. 10, 2017

(54) NANOSCALE FIELD-EFFECT TRANSISTORS FOR BIOMOLECULAR SENSORS AND OTHER APPLICATIONS

(71) Applicant: President and Fellows of Harvard College, Cambridge, MA (US)

(72) Inventors: Charles M. Lieber, Lexington, MA (US); Hwan Sung Choe, Cambridge, MA (US); Xueliang Liu, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/427,484

(22) PCT Filed: Sep. 12, 2013

(86) PCT No.: PCT/US2013/059454
§ 371 (c)(1),
(2) Date: Mar. 11, 2015

(87) PCT Pub. No.: WO2014/043341
PCT Pub. Date: Mar. 20, 2014

(65) Prior Publication Data
US 2015/0212039 A1 Jul. 30, 2015

Related U.S. Application Data

(60) Provisional application No. 61/700,201, filed on Sep. 12, 2012.

(51) Int. Cl.
*G01N 27/414* (2006.01)
*H04N 1/00* (2006.01)
(Continued)

(52) U.S. Cl.
CPC ...... *G01N 27/4146* (2013.01); *G01N 27/4145* (2013.01); *G01N 33/573* (2013.01);
(Continued)

(58) Field of Classification Search
None
See application file for complete search history.

(56) References Cited

U.S. PATENT DOCUMENTS 7,129,554 B2  10/2006  Lieber et al.
7,211,464 B2   5/2007  Lieber et al.
(Continued)

FOREIGN PATENT DOCUMENTS

CN   1926427 A    3/2007
CN   102113104 A  6/2011
(Continued)

OTHER PUBLICATIONS

U.S. Appl. No. 12/225,142, filed Mar. 11, 2009, Patolsky et al.
(Continued)

*Primary Examiner* — Robert T Crow
(74) *Attorney, Agent, or Firm* — Wolf, Greenfield & Sacks, P.C.

(57) ABSTRACT

The present invention generally relates to nanoscale wires, including to nanoscale wires used as sensors. In some cases, the nanoscale wires may be used to directly determine analytes, even within relatively complicated environments such as blood, unlike many prior art techniques. In some aspects, the nanoscale wire form at least a portion of the gate of a field-effect transistor, and in certain aspects, different periodically-varying voltages or other electrical signals may be applied to the field-effect transistor. For example, in one set of embodiments, sinusoidally-varying voltages of different frequencies may be applied to the nanoscale wire and the source electrode of the field-effect transistor. The electrical
(Continued)

conductance or other properties of the nanoscale wire in response to the periodically-varying voltages may then be determined and used to determine binding of the species.

21 Claims, 2 Drawing Sheets (51) Int. Cl.
G01N 33/573 (2006.01)
H03K 17/687 (2006.01)

(52) U.S. Cl.
CPC ....... *H03K 17/687* (2013.01); *H04N 1/00196* (2013.01); *H04N 1/00198* (2013.01); *H04N 1/00204* (2013.01); *G01N 2333/96433* (2013.01)

(56) References Cited

U.S. PATENT DOCUMENTS

| 7,301,199 | B2 | 11/2007 | Lieber et al. |
| 8,232,584 | B2 | 7/2012 | Lieber et al. |
| 8,575,663 | B2 | 11/2013 | Lieber et al. |
| 9,102,521 | B2 | 8/2015 | Lieber et al. |
| 9,297,796 | B2 | 3/2016 | Tian et al. |
| 2006/0204428 | A1 | 9/2006 | Noy et al. |
| 2007/0132043 | A1* | 6/2007 | Bradley ............... B82Y 10/00 257/414 |
| 2007/0178477 | A1* | 8/2007 | Joiner, Jr. ............ C12Q 1/6825 435/6.11 |
| 2007/0264623 | A1 | 11/2007 | Wang et al. |
| 2009/0004852 | A1 | 1/2009 | Lieber et al. |
| 2009/0299213 | A1 | 12/2009 | Patolsky et al. |
| 2010/0087013 | A1 | 4/2010 | Lieber et al. |
| 2010/0112546 | A1 | 5/2010 | Lieber et al. |
| 2010/0152057 | A1 | 6/2010 | Lieber et al. |
| 2012/0267604 | A1 | 10/2012 | Tian et al. |
| 2014/0080139 | A1 | 3/2014 | Lieber et al. |
| 2014/0184196 | A1 | 7/2014 | Lieber et al. |
| 2015/0137794 | A1 | 5/2015 | Lieber et al. |
| 2015/0351691 | A1 | 12/2015 | Lieber et al. |
| 2016/0033498 | A1 | 2/2016 | Lieber et al. |

FOREIGN PATENT DOCUMENTS

| CN | 102150037 A | 8/2011 |
| CN | 102375007 A | 3/2012 |
| WO | WO 2005/088289 A1 | 9/2005 |
| WO | WO 2011/038228 A1 | 3/2011 |

OTHER PUBLICATIONS

U.S. Appl. No. 12/308,207, filed Dec. 16, 2009, Lieber et al.
U.S. Appl. No. 14/030,170, filed Sep. 18, 2013, Gao et al.
U.S. Appl. No. 13/497,852, filed Jul. 2, 2012, Tian et al.
U.S. Appl. No. 14/124,816, filed Mar. 6, 2014, Lieber et al.
U.S. Appl. No. 14/396,542, filed Oct. 23, 2014, Lieber et al.
U.S. Appl. No. 14/423,240, filed Feb. 25, 2015, Lieber et al.
International Search Report and Written Opinion mailed Jan. 2, 2014 in connection with Application No. PCT/US2013/059454.
International Preliminary Report on Patentability mailed Mar. 26, 2015 in connection with Application No. PCT/US2013/059454.
Ping et al., Local electrical potential detection of DNA by nanowire-nanopore sensors. Nat Nanotechnol. 2011;7(2):119-125.
Timko et al., Electrical recording from hearts with flexible nanowire device arrays. Nano Lett. 2009;9(2):914-918.
Zheng et al., Nanowire biosensors for label-free, real-time, ultrasensitive protein detection. Methods Mol Biol. 2011;790:223-237.
Chinese Office Action and English Translation thereof mailed Mar. 28, 2016 for CN 201380056145.7.
Kong et al., CMOS-compatible, label-free silicon-nanowire biosensors to detect cardiac troponin I for acute myocardial infarction diagnosis. Biosens Bioelectron. Apr. 15, 2012;34(1):267-72. doi: 10.1016/j.bios.2012.02.019. Epub Feb. 19, 2012.
U.S. Appl. No. 14/788,134, filed Jun. 30, 2015, Lieber et al.
U.S. Appl. No. 15/047,267, filed Feb. 18, 2016, Lieber et al.
CN201380056145.7, Mar. 28, 2016, Chinese Office Action and English Translation thereof.

* cited by examiner

Fig. 2B

NANOSCALE FIELD-EFFECT TRANSISTORS FOR BIOMOLECULAR SENSORS AND OTHER APPLICATIONS

RELATED APPLICATIONS

This application is a U.S. National Stage application of PCT/US2013/059454, filed Sep. 12, 2013, entitled "Nanoscale Field-Effect Transistors for Biomolecular Sensors and Other Applications," which claims the benefit of U.S. Provisional Patent Application Ser. No. 61/700,201, filed Sep. 12, 2012, entitled "Nanoscale Field-Effect Transistors for Biomolecular Sensors and Other Applications," by Lieber, et al., incorporated herein by reference in its entirety.

FIELD

The present invention generally relates to nanoscale wires, including to nanoscale wires used as sensors.

BACKGROUND

Interest in nanotechnology, in particular sub-microelectronic technologies such as semiconductor quantum dots and nanowires, has been motivated by the challenges of chemistry and physics at the nanoscale, and by the prospect of utilizing these structures in electronic and related devices. Nanoscopic articles might be well-suited for transport of charge carriers and excitons (e.g. electrons, electron pairs, etc.) and thus may be useful as building blocks in nanoscale electronics applications. Nanoscale wires are well-suited for efficient transport of charge carriers and excitons, and thus are expected to be important building blocks for nanoscale electronics and optoelectronics.

Nanoscale wires having selectively functionalized surfaces have been described in, e.g., U.S. Pat. No. 7,129,554, issued Oct. 31, 2006, entitled "Nanosensors," by Lieber, et al., incorporated herein by reference in its entirety. As described, functionalization of a nanoscale wire may permit interaction of the functionalized nanoscale wire with various entities, such as molecular entities, and the interaction induces a change in a property of the functionalized nanoscale wire, which provides a mechanism for a nanoscale sensor device for detecting the presence or absence of an analyte suspected to be present in a sample.

However, it can be difficult to determine when an analyte has interacted with a functionalized nanowire in a relatively "noisy" environment, for example, when the analyte is present in a physiological fluid such as blood. The presence of salt, ions, proteins, carbohydrates, etc. within such environments can make it difficult or impossible to identify when an analyte has bound to or otherwise interacted with the nanoscale wire. Accordingly, improvements in such technologies are still needed.

SUMMARY

The present invention generally relates to nanoscale wires, including to nanoscale wires used as sensors. The subject matter of the present invention involves, in some cases, interrelated products, alternative solutions to a particular problem, and/or a plurality of different uses of one or more systems and/or articles.

In one aspect, the present invention is directed to an article. In one set of embodiments, the article includes a field-effect transistor comprising a source, a gate comprising a nanoscale wire, and a drain; a first periodic voltage generator in electrical communication with the source; and a second periodic voltage generator in electrical connection with the gate. The article, in another set of embodiments, includes a field-effect transistor comprising a source, a gate comprising a nanoscale wire, and a drain; a voltage generator apparatus able to apply different voltages to the source and the gate; and a lock-in amplifier in electrical communication with the voltage generator and the drain of the field-effect transistor.

The present invention, in another aspect, is generally directed to a method. According to one set of embodiments, the method includes acts of providing a field-effect transistor comprising a source, a gate comprising a nanoscale wire, and a drain, applying a first periodic electrical signal having a first frequency to the source, and applying a second periodic electrical signal having a second frequency to the gate. In some embodiments, the second frequency is different from the first frequency.

The method, in accordance with another set of embodiments, include acts of providing a device comprising a field-effect transistor comprising a source, a gate comprising a nanoscale wire, and a drain, applying a first periodic voltage signal to the source, applying a second periodic voltage signal to the gate, determining a voltage signal produced by the drain, and determining an alteration of the gate by determining a change in the voltage signal produced by the drain.

In another aspect, the present invention encompasses methods of making one or more of the embodiments described herein, for example, nanoscale wires used as a sensor. In still another aspect, the present invention encompasses methods of using one or more of the embodiments described herein, for example, nanoscale wires used as a sensor.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

The present invention generally relates to nanoscale wires, including to nanoscale wires used as sensors. In some cases, the nanoscale wires may be used to directly determine analytes, even within relatively complicated environments such as blood, unlike many prior art techniques. For example, a nanoscale wire may be exposed to a sample of blood, and a specific protein, such as PSA, may be directly determined within the blood. In contrast, many prior art techniques would have difficulty in identifying a specific protein in a blood sample that typically would contain multiple proteins, ions, other species, etc.

In some aspects, the nanoscale wire form at least a portion of the gate of a field-effect transistor, and in certain aspects, different periodically-varying voltages or other electrical signals may be applied to the field-effect transistor. For example, in one set of embodiments, sinusoidally-varying voltages of different frequencies may be applied to the nanoscale wire and the source electrode of the field-effect transistor. The electrical conductance or other properties of the nanoscale wire in response to the periodically-varying voltages may then be determined and used to determine binding of the species.

One embodiment of the invention is now discussed with reference to FIG. 1. In this figure, sensor device 10 comprises a field-effect transistor having a source (S) 22 and a drain (D) 26, connected by a gate 24. Gate 24 is labeled "water-gate" in FIG. 1, as it is exposed to water within microfluidic channel 29. However, it should be noted that "water" is used here for illustrative purposes only, as any other suitable fluid may be used in other embodiments; for example, the fluid within microfluidic channel 29 may be an aqueous fluid, a saline solution, an organic fluid, a physiological fluid such as blood, urine, saliva, ocular fluid, etc., or the like. Gate 24 may comprise a nanoscale wire, such as a semiconductor nanowire or a carbon nanotube. In some cases, gate 24 may be a kinked nanowire. Non-limiting examples of nanoscale wires, including kinked nanowires, are discussed in more detail below.

Figure 1:
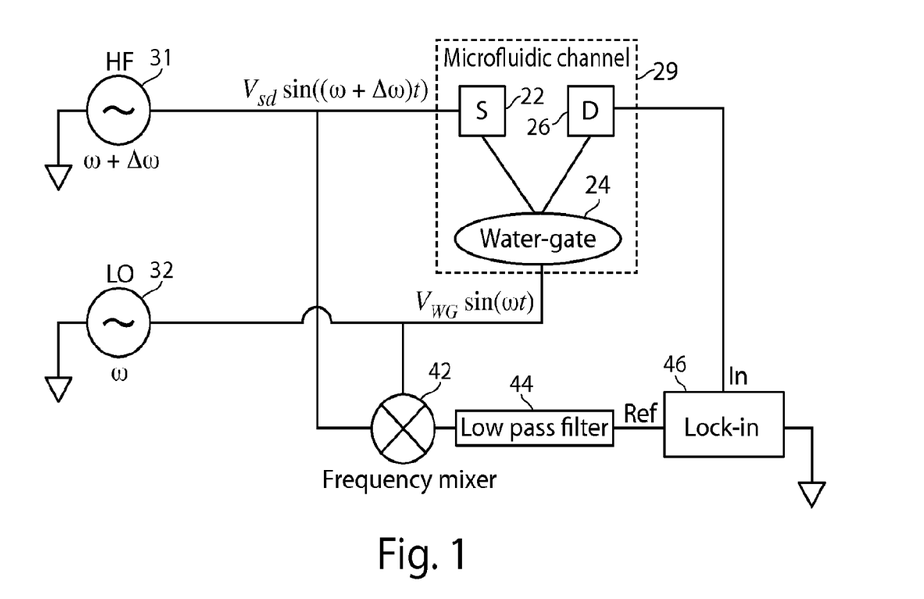
FIG. 1 schematically illustrates a sensor device in accordance with one embodiment of the invention.

In addition, FIG. 1 illustrates first voltage generator 31 and second voltage generator 32. First voltage generator 31 provides a periodically varying voltage signal to source 22 at a first frequency ($\omega+\Delta\omega$ as is shown in the figure), while second voltage generator 32 provides a periodically varying voltage signal to gate 24 at a second frequency ($\omega$). The second frequency is different from the first frequency by an amount $\Delta\omega$). Thus, the voltage applied to source 22 is $V_{sd}$ sin$((\omega+\Delta 107 )t)$, while the voltage applied to gate 24 is $V_{WG}$ sin $(\omega t)$. These voltages may be produced by first voltage generator 31 and second voltage generator 32 as is demonstrated here, or in other embodiments by other suitable voltage generator apparatuses able to produce voltages having different periods, i.e., $\omega$ and $\omega+\Delta\omega$.

Also shown in FIG. 1 is lock-in amplifier 46, which compares a reference signal produced by the voltage generators with an electrical signal from drain 26, e.g., a voltage measurement of drain 26. The reference signal is produced in FIG. 1 by mixing the frequencies from voltage generators 31 and 32 using frequency mixer 42, optionally passing the signal through a low pass filter 44, to lock-in amplifier 46. Lock-in amplifier 46 may accordingly produce an output signal based on the reference signal and the signal from the drain. Accordingly, by comparing these signals, the conductance of gate 24 may be determined.

At least a portion of gate 24 may be exposed, in some cases, to an external environment. For example, as is shown in FIG. 1, gate 24 is located within microfluidic channel 29, which may deliver a fluid to (or past) gate 24. An analyte within the fluid may bind to at least a portion of the nanoscale wire within gate 24, and such binding may cause a change in one or more electrical properties of the nanoscale wire. Accordingly, the electrical properties of gate 24 can be determined by lock-in amplifier 46, for example, as a change in an electrical property of the signal, e.g., a change in conductance, impedance, reactance, etc. Accordingly, by comparing signals from drain 26 with the reference signal, sensor device 10 in FIG. 1 can be used to determine an analyte within a fluid within microfluidic channel 29. Such determination may also be qualitative (e.g., whether the analyte is present or not), and/or quantitative (e.g., the amount and/or concentration of analyte).

The above discussion is a non-limiting example of a sensor device in accordance with one embodiment of the present invention. However, other embodiments are also possible. For instance, more generally, various aspects of the invention are directed to sensor devices and other systems and methods for determining characteristics of nanoscale wires, e.g., when exposed to an analyte. For example, the analyte may be present in any suitable fluid, including fluids with other species present in addition to the analyte.

In one aspect of the present invention, the nanoscale wire may be part of a transistor, such as a field-effect transistor. Typically, in a field-effect transistor, charge carriers such as electrons flow from a source electrode (or just "source") to a drain electrode (or just "drain"). The source and drain are typically connected by a semiconductive pathway, termed the "gate," and various properties of the gate may be used to control the flow of charge carriers between the source and the drain. For example, a gate exhibiting higher conductance may promote current flow between the source and the drain, while a gate exhibiting higher resistance (or lower conductance) may inhibit such current flow.

In addition, the electrical behavior of the gate may be controlled, at least in part, by the electrical and physical environment that the gate is exposed to. Thus, for example, the conductance of the gate may be controlled by applying a suitable voltage or potential to the gate, and/or the conductance of the gate may be affected by various molecules and/or ions proximate to the gate. For example, an analyte binding a portion of the gate, or positioned proximate the gate, may cause an alteration in the electrical behavior of the gate, which can be determined as is discussed below.

The gate may comprise one or more nanoscale wires, for example, silicon nanowires. In some cases, as is discussed below, the silicon nanowire (or other nanoscale wire) may be bent or kinked, although in other cases, the nanoscale wire need not be bent or kinked. Thus, in some embodiments, a nanoscale wire may be exposed to a suitable analyte, and the analyte may interact in some fashion with the nanoscale wire, altering an electrical property of the nanoscale wire, and thus the gate. For example, the analyte may bind nonspecifically to the nanoscale wire, or a reaction entity able to bind or interact with the analyte may be bound to a surface of the nanoscale wire, and/or positioned relative to the nanoscale wire such that an analyte can interact with the reaction entity to cause a change in an electrical property of the nanoscale wire.

In one set of embodiments, periodic electrical signals are applied to the field-effect transistor. The electrical signal may be, for instance, a voltage signal, a current signal, or the like. The periodic signal may be any signal that repeats on a regular timeframe or period. The periodic signal may be, for example, a sine wave, a triangular wave, a square wave, a sawtooth wave, or the like. In some embodiments, more than one periodic electrical signal may be applied to a field-effect transistor; for example, a first periodic electrical signal having a first frequency may be applied to the source, while a second periodic electrical signal having a second frequency may be applied to the gate.

The first frequency and the second frequency typically are different, although their differences may be relatively small. For example, the first frequency and the second frequency differ by no more than about 10%, no more than about 5%, no more than about 3%, no more than about 1%, no more than about 0.5%, no more than about 0.3%, no more than about 0.1%, no more than about 0.05%, no more than about 0.03%, or no more than about 0.01%, e.g., relative to the larger of the first frequency and the second frequency. In some embodiments, the first frequency and the second frequency differ by no more than about 10 kHz, no more than about 5 kHz, no more than about 3 kHz, no more than about 1 kHz, no more than about 500 Hz, no more than about 300 Hz, no more than about 100 Hz, no more than about 50 Hz, no more than about 30 Hz, no more than about 10 Hz, no more than about 5 Hz, no more than about 3 Hz, or no more than about 1 Hz in some cases.

The periodic electrical signals can be applied to the source and drain by any suitable electrical generator, such as a current generator or a voltage generator. One or more voltage generators may be used to apply a first periodic voltage signal to the source and a second periodic voltage signal to the gate, or one or more current generators may be used to apply a first periodic current to the source and a second current to the gate. The signals may be applied simultaneously in some cases. Thus, for example, a first voltage generator may be used to generate a first periodic voltage that is applied to the source, while a second voltage generator may be used to generate a second periodic voltage that is applied to the gate. The various electrical generators can be part of the same apparatus in some cases. The electrical generators may produce fixed periodic signals, or periodic signals that can be altered (e.g., in frequency, shape, intensity, etc.) as needed. Electrical generators for producing current and/or voltage can be readily obtained commercially.

After applying suitable electrical signals to the source and the drain, the voltage or other electrical behavior of the drain may consequently be determined, and used to determine the electrical behavior of the gate, and/or the electrical behavior of the nanoscale wire forming at least a portion of the gate. The behavior of the gate or the nanoscale wire may depend, at least in part, on the surrounding physical environment, and this may be influenced, for example, by an analyte that is able to interact in some fashion with the nanoscale wire, as previously discussed.

Thus, for example, in one set of embodiments, the voltage or other electrical behavior of the drain may be determined by comparing it against a reference signal, e.g., using a lock-in amplifier, an oscilloscope, or other device able to measure a periodic electrical signal, for example, the amplitude and/or phase shift of the signal. Generally, a lock-in amplifier mixes the signals produced by the drain and the reference to extract a signal (e.g., produced by the field-effect transistor), which can be subsequently analyzed, e.g., to determine an electrical property of the gate and/or the nanoscale wire. The reference signal can be created, in one set of embodiments, by mixing the electrical signals produced by the voltage or other electrical generators, before such signals interact with the field effect transistor. For example, the electrical signals may be combined using a frequency mixer. The signal may also be processed using a low-pass filter prior to being delivered to the lock-in amplifier (or in some cases, the low-pass filter and/or the frequency mixer may be part of the lock-in amplifier). Frequency mixers, low-pass filters, and lock-in amplifiers may be obtained from commercial sources. In addition, all of the voltages discussed herein are typically measured relative to ground, e.g., the lock-in amplifier may be grounded and all voltages measured relative thereto.

Without wishing to be bound by any theory, the conductance of the nanoscale wire and/or the gate within the field effect transistor may be determined by determining the voltage of the drain (e.g., phase and/or amplitude) using the lock-in amplifier and the periods of the voltage generators.

As the electrical behavior of the nanoscale wire may be controlled, at least in part, by the environment surrounding the nanoscale wire, the nanoscale wire may be used as a sensor in accordance with certain embodiments of the invention. For example, the nanoscale wire may be used to determine an analyte in a fluid surrounding the nanoscale wire. In some cases, a reaction entity able to bind or interact with the analyte may be bound to a surface of the nanoscale wire, and/or positioned relative to the nanoscale wire, such that binding or interaction of the analyte to the reaction entity causes a determinable change in the nanoscale wire. Such a reaction entity may be used to determine a variety of potential analytes, and such determinations may be made qualitatively or quantitatively. For instance, the presence, amount, and/or concentration of an analyte in the fluid may be determined, in various embodiments, e.g., by determining an electrical property of the nanoscale wire, such as conductance or impedance. Non-limiting examples of such reaction entities are discussed in greater detail below.

As mentioned, the nanoscale wire itself may be any suitable nanoscale wire that can interact with an analyte, and/or that can be modified such that a reaction entity able to bind or interact with the analyte may be bound to a surface of the nanoscale wire, and/or positioned relative to the nanoscale wire. Non-limiting examples of suitable nanoscale wires include carbon nanotubes, nanorods, nanowires, organic and inorganic conductive and semiconducting polymers, metal nanoscale wires, semiconductor nanoscale wires (for example, formed from silicon), and the like. If carbon nanotubes are used, they may be single-walled and/or multi-walled, and may be metallic and/or semiconducting in nature. Other conductive or semiconducting elements that may not be nanoscale wires, but are of various small nanoscopic-scale dimension, also can be used in certain embodiments.

In general, a "nanoscale wire" (also known herein as a "nanoscopic-scale wire" or "nanoscopic wire") generally is a wire or other nanoscale object, that at any point along its length, has at least one cross-sectional dimension and, in some embodiments, two orthogonal cross-sectional dimensions (e.g., a diameter) of less than 1 micrometer, less than about 500 nm, less than about 200 nm, less than about 150 nm, less than about 100 nm, less than about 70, less than about 50 nm, less than about 20 nm, less than about 10 nm, less than about 5 nm, than about 2 nm, or less than about 1 nm. In some embodiments, the nanoscale wire is generally cylindrical. In other embodiments, however, other shapes are possible; for example, the nanoscale wire can be faceted, i.e., the nanoscale wire may have a polygonal cross-section. The cross-section of a nanoscale wire can be of any arbitrary shape, including, but not limited to, circular, square, rectangular, annular, polygonal, or elliptical, and may be a regular or an irregular shape. The nanoscale wire can also be solid or hollow.

In some cases, the nanoscale wire has one dimension that is substantially longer than the other dimensions of the nanoscale wire. For example, the nanoscale wire may have a longest dimension that is at least about 1 micrometer, at least about 3 micrometers, at least about 5 micrometers, or at least about 10 micrometers or about 20 micrometers in length, and/or the nanoscale wire may have an aspect ratio (longest dimension to shortest orthogonal dimension) of greater than about 2:1, greater than about 3:1, greater than about 4:1, greater than about 5:1, greater than about 10:1, greater than about 25:1, greater than about 50:1, greater than about 75:1, greater than about 100:1, greater than about 150:1, greater than about 250:1, greater than about 500:1, greater than about 750:1, or greater than about 1000:1 or more in some cases.

In some embodiments, a nanoscale wire are substantially uniform, or have a variation in average diameter of the nanoscale wire of less than about 30%, less than about 25%, less than about 20%, less than about 15%, less than about 10%, or less than about 5%. For example, the nanoscale wires may be grown from substantially uniform nanoclusters or particles, e.g., colloid particles. See, e.g., U.S. Pat. No. 7,301,199, issued Nov. 27, 2007, entitled "Nanoscale Wires and Related Devices," by Lieber, et al., incorporated herein by reference in its entirety. In some cases, the nanoscale wire may be one of a population of nanoscale wires having an average variation in diameter, of the population of nanowires, of less than about 30%, less than about 25%, less than about 20%, less than about 15%, less than about 10%, or less than about 5%.

In some embodiments, a nanoscale wire has a conductivity of or of similar magnitude to any semiconductor or any metal. The nanoscale wire can be formed of suitable materials, e.g., semiconductors, metals, etc., as well as any suitable combinations thereof. In some cases, the nanoscale wire will have the ability to pass electrical charge, for example, being electrically conductive. For example, the nanoscale wire may have a relatively low resistivity, e.g., less than about $10^{-3}$ Ohm m, less than about $10^{-4}$ Ohm m, less than about $10^{-6}$ Ohm m, or less than about $10^{-7}$ Ohm m. The nanoscale wire can, in some embodiments, have a conductance of at least about 1 microsiemens, at least about 3 microsiemens, at least about 10 microsiemens, at least about 30 microsiemens, or at least about 100 microsiemens.

The nanoscale wire can be solid or hollow, in various embodiments. As used herein, a "nanotube" is a nanoscale wire that is hollow, or that has a hollowed-out core, including those nanotubes known to those of ordinary skill in the art. As another example, a nanotube may be created by creating a core/shell nanowire, then etching away at least a portion of the core to leave behind a hollow shell. Accordingly, in one set of embodiments, the nanoscale wire is a non-carbon nanotube. In contrast, a "nanowire" is a nanoscale wire that is typically solid (i.e., not hollow). Thus, in one set of embodiments, the nanoscale wire may be a semiconductor nanowire, such as a silicon nanowire.

In one set of embodiment, a nanoscale wire may comprise or consist essentially of a metal. Non-limiting examples of potentially suitable metals include aluminum, gold, silver, copper, molybdenum, tantalum, titanium, nickel, tungsten, chromium, or palladium. In another set of embodiments, a nanoscale wire comprises or consists essentially of a semiconductor. Typically, a semiconductor is an element having semiconductive or semi-metallic properties (i.e., between metallic and non-metallic properties). An example of a semiconductor is silicon. Other non-limiting examples include elemental semiconductors, such as gallium, germanium, diamond (carbon), tin, selenium, tellurium, boron, or phosphorous. In other embodiments, more than one element may be present in the nanoscale wire as the semiconductor, for example, gallium arsenide, gallium nitride, indium phosphide, cadmium selenide, etc. Still other examples include a Group II-VI material (which includes at least one member from Group II of the Periodic Table and at least one member from Group VI, for example, ZnS, ZnSe, ZnSSe, ZnCdS, CdS, or CdSe), or a Group III-V material (which includes at least one member from Group III and at least one member from Group V, for example GaAs, GaP, GaAsP, InAs, InP, AlGaAs, or InAsP).

In certain embodiments, the semiconductor can be undoped or doped (e.g., p-type or n-type). For example, in one set of embodiments, a nanoscale wire may be a p-type semiconductor nanoscale wire or an n-type semiconductor nanoscale wire, and can be used as a component of a transistor such as a field effect transistor ("FET"). For instance, the nanoscale wire may act as the "gate" of a source-gate-drain arrangement of a FET, while metal leads or other conductive pathways (as discussed herein) are used as the source and drain electrodes.

In some embodiments, a dopant or a semiconductor may include mixtures of Group IV elements, for example, a mixture of silicon and carbon, or a mixture of silicon and germanium. In other embodiments, the dopant or the semiconductor may include a mixture of a Group III and a Group V element, for example, BN, BP, BAs, AN, AlP, AlAs, AlSb, GaN, GaP, GaAs, GaSb, InN, InP, InAs, or InSb. Mixtures of these may also be used, for example, a mixture of BN/BP/BAs, or BN/AlP. In other embodiments, the dopants may include alloys of Group III and Group V elements. For example, the alloys may include a mixture of AlGaN, GaPAs, InPAs, GaInN, AlGaInN, GaInAsP, or the like. In other embodiments, the dopants may also include a mixture of Group II and Group VI semiconductors. For example, the semiconductor may include ZnO, ZnS, ZnSe, ZnTe, CdS, CdSe, CdTe, HgS, HgSe, HgTe, BeS, BeSe, BeTe, MgS, MgSe, or the like. Alloys or mixtures of these dopants are also be possible, for example, (ZnCd)Se, or Zn(SSe), or the like. Additionally, alloys of different groups of semiconductors may also be possible, for example, a combination of a Group II-Group VI and a Group III-Group V semiconductor, for example, $(GaAs)_x(ZnS)_{1-x}$. Other examples of dopants may include combinations of Group IV and Group VI elements, such as GeS, GeSe, GeTe, SnS, SnSe, SnTe, PbO, PbS, PbSe, or PbTe. Other semiconductor mixtures may include a combination of a Group I and a Group VII, such as CuF, CuCl, CuBr, Cut AgF, AgCl, AgBr, AgI, or the like. Other dopant compounds may include different mixtures of these elements, such as $BeSiN_2$, $CaCN_2$, $ZnGeP_2$, $CdSnAs_2$, $ZnSnSb_2$, $CuGeP_3$, $CuSi_2P_3$, $Si_3N_4$, $Ge_3N_4$, $Al_2O_3$, $(Al, Ga, In)_2(S, Se, Te)_3$, $Al_2CO$, $(Cu, Ag)(Al, Ga, In, Tl, Fe)(S, Se, Te)_2$ and the like.

The doping of the semiconductor to produce a p-type or n-type semiconductor may be achieved via bulk-doping in certain embodiments, although in other embodiments, other doping techniques (such as ion implantation) can be used. Many such doping techniques that can be used will be familiar to those of ordinary skill in the art, including both bulk doping and surface doping techniques. A bulk-doped article (e.g. an article, or a section or region of an article) is an article for which a dopant is incorporated substantially throughout the crystalline lattice of the article, as opposed to an article in which a dopant is only incorporated in particular regions of the crystal lattice at the atomic scale, for example, only on the surface or exterior. For example, some articles are typically doped after the base material is grown, and thus the dopant only extends a finite distance from the surface or exterior into the interior of the crystalline lattice. It should be understood that "bulk-doped" does not define or reflect a concentration or amount of doping in a semiconductor, nor does it necessarily indicate that the doping is uniform. "Heavily doped" and "lightly doped" are terms the meanings of which are clearly understood by those of ordinary skill in the art. In some embodiments, one or more regions comprise a single monolayer of atoms ("delta-doping"). In certain cases, the region may be less than a single monolayer thick (for example, if some of the atoms within the monolayer are absent). As a specific example, the regions may be arranged in a layered structure within the nanoscale wire, and one or more of the regions can be delta-doped or partially delta-doped.

Accordingly, in one set of embodiments, the nanoscale wires may include a heterojunction, e.g., of two regions with dissimilar materials or elements, and/or the same materials or elements but at different ratios or concentrations. The regions of the nanoscale wire may be distinct from each other with minimal cross-contamination, or the composition of the nanoscale wire can vary gradually from one region to the next. The regions may be both longitudinally arranged relative to each other, or radially arranged (e.g., as in a core/shell arrangement) on the nanoscale wire. Each region may be of any size or shape within the wire. The junctions may be, for example, a p/n junction, a p/p junction, an n/n junction, a p/i junction (where i refers to an intrinsic semiconductor), an n/i junction, an i/i junction, or the like. The junction can also be a Schottky junction in some embodiments. The junction may also be, for example, a semiconductor/semiconductor junction, a semiconductor/metal junction, a semiconductor/insulator junction, a metal/metal junction, a metal/insulator junction, an insulator/insulator junction, or the like. The junction may also be a junction of two materials, a doped semiconductor to a doped or an undoped semiconductor, or a junction between regions having different dopant concentrations. The junction can also be a defected region to a perfect single crystal, an amorphous region to a crystal, a crystal to another crystal, an amorphous region to another amorphous region, a defected region to another defected region, an amorphous region to a defected region, or the like. More than two regions may be present, and these regions may have unique compositions or may comprise the same compositions. As one example, a wire can have a first region having a first composition, a second region having a second composition, and a third region having a third composition or the same composition as the first composition. Non-limiting examples of nanoscale wires comprising heterojunctions (including core/shell heterojunctions, longitudinal heterojunctions, etc., as well as combinations thereof) are discussed in U.S. Pat. No. 7,301,199, issued Nov. 27, 2007, entitled "Nanoscale Wires and Related Devices," by Lieber, et al., incorporated herein by reference in its entirety.

In some embodiments, the nanoscale wire is a bent or a kinked nanoscale wire. A kink is typically a relatively sharp transition or turning between a first substantially straight portion of a wire and a second substantially straight portion of a wire. For example, a nanoscale wire may have 1, 2, 3, 4, or 5 or more kinks. In some cases, the nanoscale wire is formed from a single crystal and/or comprises or consists essentially of a single crystallographic orientation, for example, a <110> crystallographic orientation, a <112> crystallographic orientation, or a <11$\bar{2}$0> crystallographic orientation. It should be noted that the kinked region need not have the same crystallographic orientation as the rest of the semiconductor nanoscale wire. In some embodiments, a kink in the semiconductor nanoscale wire may be at an angle of about 120° or a multiple thereof. The kinks can be intentionally positioned along the nanoscale wire in some cases. For example, a nanoscale wire may be grown from a catalyst particle by exposing the catalyst particle to various gaseous reactants to cause the formation of one or more kinks within the nanoscale wire. Non-limiting examples of kinked nanoscale wires, and suitable techniques for making such wires, are disclosed in International Patent Application No. PCT/US2010/050199, filed Sep. 24, 2010, entitled "Bent Nanowires and Related Probing of Species," by Tian, et al., published as WO 2011/038228 on Mar. 31, 2011, incorporated herein by reference in its entirety.

In one set of embodiments, the nanoscale wire is formed from a single crystal, for example, a single crystal nanoscale wire comprising a semiconductor. A single crystal item may be formed via covalent bonding, ionic bonding, or the like, and/or combinations thereof. While such a single crystal item may include defects in the crystal in some cases, the single crystal item is distinguished from an item that includes one or more crystals, not ionically or covalently bonded, but merely in close proximity to one another.

In some embodiments, the nanoscale wires used herein are individual or free-standing nanoscale wires. For example, an "individual" or a "free-standing" nanoscale wire may, at some point in its life, not be attached to another article, for example, with another nanoscale wire, or the free-standing nanoscale wire may be in solution. This is in contrast to nanoscale features etched onto the surface of a substrate, e.g., a silicon wafer, in which the nanoscale features are never removed from the surface of the substrate as a free-standing article. This is also in contrast to conductive portions of articles which differ from surrounding material only by having been altered chemically or physically, in situ, i.e., where a portion of a uniform article is made different from its surroundings by selective doping, etching, etc. An "individual" or a "free-standing" nanoscale wire is one that can be (but need not be) removed from the location where it is made, as an individual article, and transported to a different location and combined with different components to make a functional device such as those described herein and those that would be contemplated by those of ordinary skill in the art upon reading this disclosure.

The nanoscale wire, in some embodiments, may be responsive to a property external of the nanoscale wire, e.g., a chemical property, an electrical property, a physical property, etc. Such determination may be qualitative and/or quantitative. For example, in one set of embodiments, the nanoscale wire may be responsive to voltage. For instance, the nanoscale wire may exhibits a voltage sensitivity of at least about 5 microsiemens/V; by determining the conductivity of a nanoscale wire, the voltage surrounding the nanoscale wire may thus be determined. In other embodiments, the voltage sensitivity can be at least about 10 microsiemens/V, at least about 30 microsiemens/V, at least about 50 microsiemens/V, or at least about 100 microsiemens/V. Other examples of electrical properties that can be determined include resistance, resistivity, conductance, conductivity, impendence, or the like.

As another example, a nanoscale wire may be responsive to a chemical property of the environment surrounding the nanoscale wire. For example, an electrical property of the nanoscale wire can be affected by a chemical environment surrounding the nanoscale wire, and the electrical property can be thereby determined to determine the chemical environment surrounding the nanoscale wire. As a specific non-limiting example, the nanoscale wires may be sensitive to pH or hydrogen ions. Further non-limiting examples of such nanoscale wires are discussed in U.S. Pat. No. 7,129, 554, filed Oct. 31, 2006, entitled "Nanosensors," by Lieber, et al., incorporated herein by reference in its entirety.

As a non-limiting example, the nanoscale wire may have the ability to bind to an analyte indicative of a chemical property of the environment surrounding the nanoscale wire (e.g., hydrogen ions for pH, or concentration for an analyte of interest), and/or the nanoscale wire may be partially or fully functionalized, i.e. comprising surface functional moieties, to which an analyte is able to bind, thereby causing a determinable property change to the nanoscale wire, e.g., a change to the resistivity or impedance of the nanoscale wire. The binding of the analyte can be specific or non-specific. Functional moieties may include simple groups, selected from the groups including, but not limited to, —OH, —CHO, —COOH, —SO$_3$H, —CN, —NH$_2$, —SH, —COSH, —COOR, halide; biomolecular entities including, but not limited to, amino acids, proteins, sugars, DNA, antibodies, antigens, and enzymes; grafted polymer chains with chain length less than the diameter of the nanowire core, selected from a group of polymers including, but not limited to, polyamide, polyester, polyimide, polyacrylic; a shell of material comprising, for example, metals, semiconductors, and insulators, which may be a metallic element, an oxide, an sulfide, a nitride, a selenide, a polymer and a polymer gel. A non-limiting example of a protein is PSA (prostate specific antigen), which can be determined, for example, by modifying the nanoscale wires by binding monoclonal antibodies for PSA (Ab1) thereto. See, e.g., U.S. Pat. No. 8,232,584, issued Jul. 31, 2012, entitled "Nanoscale Sensors," by Lieber, et al., incorporated herein by reference in its entirety.

In some embodiments, a reaction entity may be bound to a surface of the nanoscale wire, and/or positioned in relation to the nanoscale wire such that the analyte can be determined by determining a change in a property of the nanoscale wire. The "determination" may be quantitative and/or qualitative, depending on the application. The term "reaction entity" refers to any entity that can interact with an analyte in such a manner to cause a detectable change in a property (such as an electrical property) of a nanoscale wire. The reaction entity may enhance the interaction between the nanowire and the analyte, or generate a new chemical species that has a higher affinity to the nanowire, or to enrich the analyte around the nanowire. The reaction entity can comprise a binding partner to which the analyte binds. The reaction entity, when a binding partner, can comprise a specific binding partner of the analyte. For example, the reaction entity may be a nucleic acid, an antibody, a sugar, a carbohydrate or a protein. Alternatively, the reaction entity may be a polymer, catalyst, or a quantum dot. A reaction entity that is a catalyst can catalyze a reaction involving the analyte, resulting in a product that causes a detectable change in the nanowire, e.g. via binding to an auxiliary binding partner of the product electrically coupled to the nanowire. Another exemplary reaction entity is a reactant that reacts with the analyte, producing a product that can cause a detectable change in the nanowire. The reaction entity can comprise a shell on the nanowire, e.g. a shell of a polymer that recognizes molecules in, e.g., a gaseous sample, causing a change in conductivity of the polymer which, in turn, causes a detectable change in the nanowire.

The term "binding partner" refers to a molecule that can undergo binding with a particular analyte, or "binding partner" thereof, and includes specific, semi-specific, and non-specific binding partners as known to those of ordinary skill in the art. The term "specifically binds," when referring to a binding partner (e.g., protein, nucleic acid, antibody, etc.), refers to a reaction that is determinative of the presence and/or identity of one or other member of the binding pair in a mixture of heterogeneous molecules (e.g., proteins and other biologics). Thus, for example, in the case of a receptor/ligand binding pair the ligand would specifically and/or preferentially select its receptor from a complex mixture of molecules, or vice versa. An enzyme would specifically bind to its substrate, a nucleic acid would specifically bind to its complement, an antibody would specifically bind to its antigen. Other examples include, nucleic acids that specifically bind (hybridize) to their complement, antibodies specifically bind to their antigen, and the like. The binding may be by one or more of a variety of mechanisms including, but not limited to ionic interactions, and/or covalent interactions, and/or hydrophobic interactions, and/or van der Waals interactions, etc.

The antibody may be any protein or glycoprotein comprising or consisting essentially of one or more polypeptides substantially encoded by immunoglobulin genes or fragments of immunoglobulin genes. Examples of recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50 70 kD). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well characterized fragments produced by digestion with various peptidases. Thus, for example, pepsin digests an antibody below (i.e. toward the Fc domain) the disulfide linkages in the hinge region to produce F(ab)'$_2$, a dimer of Fab which itself is a light chain joined to $V_H C_{H1}$ by a disulfide bond. The F(ab)'$_2$ may be reduced under mild conditions to break the disulfide linkage in the hinge region thereby converting the (Fab)$_2$ dimer into an Fab' monomer. The Fab' monomer is essentially a Fab with part of the hinge region. While various antibody fragments are defined in terms of the digestion of an intact antibody, one of skill will appreciate that such fragments may be synthesized de novo either chemically, by utilizing recombinant DNA methodology, or by "phage display" methods. Non-limiting examples of antibodies include single chain antibodies, e.g., single chain Fv (scFv) antibodies in which a variable heavy and a variable light chain are joined together (directly or through a peptide linker) to form a continuous polypeptide.

The analyte may be present in a fluid surrounding the nanoscale wire, and the fluid may be any suitable fluid able to contain the analyte. For example, the fluid may be water, a saline solution, an aqueous solution, an organic fluid, or the like. The fluid may be a liquid, a gas, a viscoelastic material, or the like. The fluid may also contain any salts and/or ions at any suitable amount or concentration, e.g., in addition to the analyte. In some embodiments, the fluid is a physiological fluid such as whole blood, serum or plasma or other blood fractions, urine, ocular fluid, saliva, cerebro-spinal fluid, fluid or other samples from tonsils, lymph nodes, etc.

The fluid may be delivered to the nanoscale wire, such that the nanoscale wire is exposed to the fluid, using any suitable mechanism. For example, the nanoscale wire may be positioned on a substrate, at least a portion of which is exposed to the fluid. For instance, a drop of the fluid may be placed on a region (e.g., a sample region) containing the nanoscale wire, or the fluid may be delivered to the nanoscale wire using a channel such as a microfluidic channel. Thus, for example, a fluid suspected of containing an analyte may be delivered via the channel to the nanoscale wire, and the analyte may bind or otherwise interact with the nanoscale wire, as discussed herein.

"Microfluidic," as used herein, refers to a device, article, or system including at least one fluid channel having a cross-sectional dimension of less than about 1 mm. Thus, for example, one or more microfluidic channels may be present on or in a suitable substrate. The "cross-sectional dimension" of the channel is measured perpendicular to the direction of net fluid flow within the channel. Thus, for example, some or all of the fluid channels can have a maximum cross-sectional dimension less than about 2 mm, and in certain cases, less than about 1 mm. In one set of embodiments, all of the fluid channels are microfluidic and/or have a largest cross sectional dimension of no more than about 2 mm or about 1 mm. In certain embodiments, the fluid channels may be formed in part by a single component (e.g. an etched substrate or molded unit). Of course, larger channels, tubes, chambers, reservoirs, etc. can be used to store fluids and/or deliver fluids to the nanoscale wires, and/or other various elements or systems, in other embodiments of the invention.

In one set of embodiments, the maximum cross-sectional dimension of the channels is less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 20 micrometers, less than about 15 micrometers, less than about 10 micrometers, less than about 5 micrometers, less than about 3 micrometers, less than about 2 micrometers, less than about 1 micrometer, less than about 500 nm, less than about 300 nm, less than about 100 nm, or less than about 50 nm.

A channel can have any cross-sectional shape (circular, oval, triangular, irregular, square or rectangular, or the like) and be defined in a suitable substrate or other medium. The channel can be covered or uncovered. In embodiments where it is completely covered, at least one portion of the channel can have a cross-section that is completely enclosed, or the entire channel may be completely enclosed along its entire length with the exception of its inlets and/or outlets or openings. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (i.e., a concave or convex meniscus).

The channel may be of any size, for example, having a largest dimension perpendicular to net fluid flow of less than about 5 mm or 2 mm, or less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm. In some cases, the dimensions of the channel are chosen such that fluid is able to freely flow through the channel. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel may be used. For example, two or more channels may be used, where they are positioned adjacent or proximate to each other, positioned to intersect with each other, etc.

In certain embodiments, one or more of the channels may have an average cross-sectional dimension of less than about 10 cm. In certain instances, the average cross-sectional dimension of the channel is less than about 5 cm, less than about 3 cm, less than about 1 cm, less than about 5 mm, less than about 3 mm, less than about 1 mm, less than 500 micrometers, less than 200 micrometers, less than 100 micrometers, less than 50 micrometers, or less than 25 micrometers. The "average cross-sectional dimension" is measured in a plane perpendicular to net fluid flow within the channel. If the channel is non-circular, the average cross-sectional dimension may be taken as the diameter of a circle having the same area as the cross-sectional area of the channel. Thus, the channel may have any suitable cross-sectional shape, for example, circular, oval, triangular, irregular, square, rectangular, quadrilateral, or the like. In some embodiments, the channels are sized so as to allow laminar flow of one or more fluids contained within the channel to occur.

In some cases, there are a relatively large number and/or a relatively large length of channels. For example, in some embodiments, the channels, when added together, can have a total length of at least about 100 micrometers, at least about 300 micrometers, at least about 500 micrometers, at least about 1 mm, at least about 3 mm, at least about 5 mm, at least about 10 mm, at least about 30 mm, at least 50 mm, at least about 100 mm, at least about 300 mm, at least about 500 mm, at least about 1 m, at least about 2 m, or at least about 3 m in some cases. As another example, there may be at least 1 channel present, or there may be at least 3 channels, at least 5 channels, at least 10 channels, at least 20 channels, at least 30 channels, at least 40 channels, at least 50 channels, at least 70 channels, at least 100 channels, etc. present.

A variety of materials and methods, according to certain aspects of the invention, can be used to form articles, substrates, or other components such as those described herein, e.g., channels such as microfluidic channels, chambers, etc. For example, various articles, substrates, or components can be formed from solid materials, in which the channels can be formed via micromachining, film deposition processes such as spin coating and chemical vapor deposition, laser fabrication, photolithographic techniques, etching methods including wet chemical or plasma processes, and the like. See, for example, *Scientific American,* 248:44-55, 1983 (Angell, et al).

In one set of embodiments, various structures or components described herein can be formed of a polymer, for example, an elastomeric polymer such as polydimethylsiloxane ("PDMS"), polytetrafluoroethylene ("PTFE" or Teflon®), or the like. For instance, according to one embodiment, a microfluidic channel may be implemented by fabricating the fluidic system separately using PDMS or other soft lithography techniques (details of soft lithography techniques suitable for this embodiment are discussed in the references entitled "Soft Lithography," by Younan Xia and George M. Whitesides, published in the *Annual Review of Material Science*, 1998, Vol. 28, pages 153-184, and "Soft Lithography in Biology and Biochemistry," by George M. Whitesides, Emanuele Ostuni, Shuichi Takayama, Xingyu Jiang and Donald E. Ingber, published in the *Annual Review of Biomedical Engineering*, 2001, Vol. 3, pages 335-373; each of these references is incorporated herein by reference).

Other examples of potentially suitable polymers include, but are not limited to, polyethylene terephthalate (PET), polyacrylate, polymethacrylate, polycarbonate, polystyrene, polyethylene, polypropylene, polyvinylchloride, cyclic olefin copolymer (COC), polytetrafluoroethylene, a fluorinated polymer, a silicone such as polydimethylsiloxane, polyvinylidene chloride, bis-benzocyclobutene ("BCB"), a polyimide, a fluorinated derivative of a polyimide, or the like. Combinations, copolymers, or blends involving polymers including those described above are also envisioned. The device may also be formed from composite materials, for example, a composite of a polymer and a semiconductor material.

In some embodiments, various structures or components are fabricated from polymeric and/or flexible and/or elastomeric materials, and can be conveniently formed of a hardenable fluid, facilitating fabrication via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, waxes, metals, or mixtures or composites thereof heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art.

A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, dodecyltrichlorosilanes, etc.

Silicone polymers are used in certain embodiments, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying fabrication of various structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

One advantage of forming structures such as microfluidic structures or channels from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, such structures can be fabricated and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods that may be used, as well as overall molding techniques, are described in the art, for example, in an article entitled "Rapid Prototyping of Microfluidic Systems and Polydimethylsiloxane," *Anal. Chem.*, 70:474-480, 1998 (Duffy et al.), incorporated herein by reference.

The following documents are incorporated herein by reference in their entireties: U.S. Pat. No. 7,211,464, issued May 1, 2007, entitled "Doped Elongated Semiconductors, Growing Such Semiconductors, Devices Including Such Semiconductors, and Fabricating Such Devices," by Lieber, et al.; and U.S. Pat. No. 7,301,199, issued Nov. 27, 2007, entitled "Nanoscale Wires and Related Devices," by Lieber, et al.; U.S. patent application Ser. No. 10/588,833, filed Aug. 9, 2006, entitled "Nanostructures Containing Metal-Semiconductor Compounds," by Lieber, et al., published as U.S. Patent Application Publication No. 2009/0004852 on Jan. 1, 2009; U.S. patent application Ser. No. 11/629,722, filed Dec. 15, 2006, entitled "Nanosensors," by Wang, et al., published as U.S. Patent Application Publication No. 2007-0264623 on Nov. 15, 2007; U.S. patent application Ser. No. 12/308, 207, filed Dec. 9, 2008, entitled "Nanosensors and Related Technologies," by Lieber, et al.; U.S. Pat. No. 8,232,584, issued Jul. 31, 2012, entitled "Nanoscale Sensors," by Lieber, et al.; U.S. patent application Ser. No. 12/312,740, filed May 22, 2009, entitled "High-Sensitivity Nanoscale Wire Sensors," by Lieber, et al., published as U.S. Patent Application Publication No. 2010-052057 on Jun. 17, 2010; and International Patent Application No. PCT/US2010/050199, filed Sep. 24, 2010, entitled "Bent Nanowires and Related Probing of Species," by Tian, et al., published as WO 2011/038228 on Mar. 31, 2011.

The following examples are intended to illustrate certain embodiments of the present invention, but do not exemplify the full scope of the invention.

EXAMPLE 1

Nanowire field-effect transistors (NWFET) as electrochemical biosensors have been suggested in the past. See, for example, U.S. Pat. No. 7,129,554, issued Oct. 31, 2006, entitled "Nanosensors," by Lieber, et al., incorporated herein by reference in its entirety. However, despite many significant advantages for clinical diagnosis (point-of-care) and biowarfare agents detection applications, NWFET cannot yet be implemented for those in physiological conditions, due to the difficulty of a biosensor based on charge detection by the short Debye length in high ionic strength solutions.

This example illustrates a high-frequency modulation measurements with a frequency mixer for a novel kinked NWFET biosensor likely to be capable of not only point-of-care application but also in situ intracellular electrochemical biosensing. The high frequency modulation measurement, unlike conventional measurements, allows detection of significant changes in the electrical property of kinked NWFETs based on the thickness of the gate dielectric caused by target proteins, instead of based on the number of charges around the surface of nanowire. In addition, introducing AC frequency mixing of a source-drain and a gate bias allows the collection of modulated signals in relatively low frequency, in place of high frequency signals.

Figure 2A:
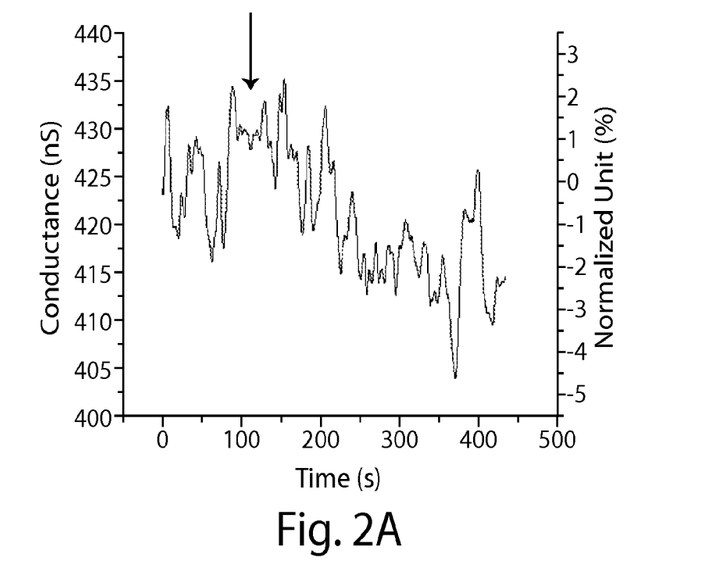
FIGS. 2A-2B illustrate use of a sensor device comprising a nanowire, in another embodiment of the invention.
Figure 2B:
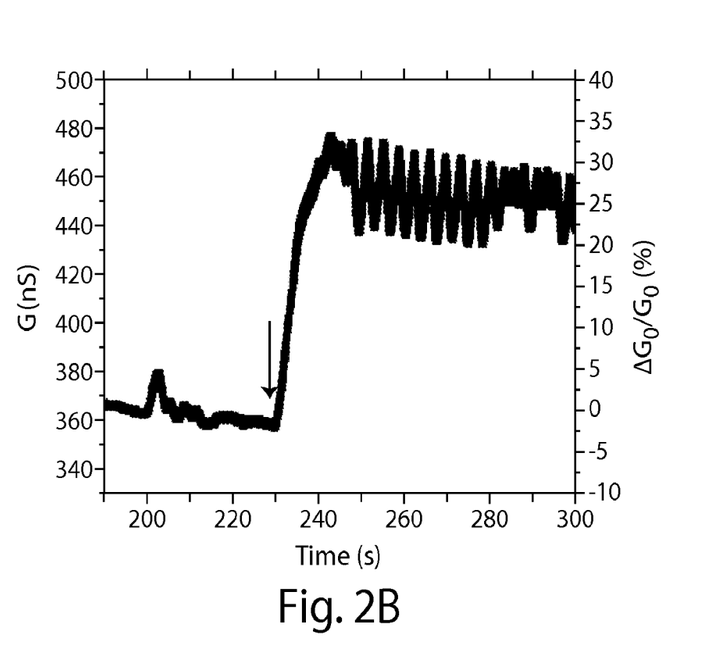

The experimental results with an n-type kinked NWFET and a p-type straight NWFET in a microfluidic chamber for prostate specific antigen (PSA) detection in PBS 1X (same ionic strength as physiological condition) are discussed in this example. While conventional 79 Hz measurements were not able to show consistent signal changes of the NWFET biosensor with in-and-out of PSA in PBS 1X, the high frequency modulation measurement with mixing technique successfully induced consistent signal change with the existence of PSA in PBS 1X solution, as can be seen in FIG. 2.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of determining an interaction of a species with a nanoscale wire, comprising:
    providing a field-effect transistor comprising a source, a gate comprising a nanoscale wire, and a drain;
    applying a first periodic electrical signal having a first frequency to the source;
    applying a second periodic electrical signal having a second frequency to the gate, wherein the second frequency is different from the first frequency; and
    determining a change in an electrical property of the gate, wherein the interaction of the species with the nanoscale wire causes the determinable change.

2. The method of claim 1, wherein the first periodic electrical signal and the second periodic electrical signal are simultaneously applied.

3. The method of claim 1, wherein the first and second periodic electrical signals are each voltages.

4. The method of claim 3, wherein the voltages are created relative to the drain.

5. The method of claim 1, wherein the first frequency and the second frequency differ by no more than 10% relative to the larger of the first frequency and the second frequency.

6. The method of claim 1, wherein the first frequency and the second frequency differ by no more than 1% relative to the larger of the first frequency and the second frequency.

7. The method of claim 1, wherein the first frequency and the second frequency differ by no more than 0.1% relative to the larger of the first frequency and the second frequency.

8. The method of claim 1, wherein the first frequency and the second frequency differ by no more than 10 kHz.

9. The method of claim 1, wherein the first frequency and the second frequency differ by no more than 1 kHz.

10. The method of claim 1, wherein the first frequency and the second frequency differ by no more than 100 Hz.

11. The method of claim 1, wherein the electrical property is conductance and/or impedance.

12. The method of claim 1, wherein the interaction of the species with the nanoscale wire causes a determinable change in the conductance of the nanoscale wire.

13. The method of claim 12, wherein the interaction is a binding interaction.

14. The method of claim 1, wherein the species is a protein.

15. The method of claim 14, wherein the protein is prostate specific antigen.

16. The method of claim 1, wherein the interaction occurs via a reaction entity able to interact with the species.

17. The method of claim 16, wherein the reaction entity is an antibody.

18. The method of claim 1, wherein the nanoscale wire has a diameter of less than 1 micrometer.

19. The method of claim 1, wherein the nanoscale wires has a variation in average diameter of less than about 20%.

20. The method of claim 1, wherein the nanoscale wire comprises a semiconductor.

21. The method of claim 1, wherein the nanoscale wire comprises silicon.

* * * * *